United States Patent [19]
Ramin

[11] Patent Number: 5,804,169
[45] Date of Patent: Sep. 8, 1998

[54] QUICK-DRYING AGENT FOR A NAIL VARNISH FILM AND DRYING PROCESS USING THE SAID AGENT

[75] Inventor: Roland Ramin, Itteville, France

[73] Assignee: L'Oreal, Paris, France

[21] Appl. No.: 565,757

[22] Filed: Nov. 30, 1995

[30] Foreign Application Priority Data

Dec. 1, 1994 [FR] France .................................. 94 14462

[51] Int. Cl.$^6$ .................. A61K 7/00; A61K 7/04
[52] U.S. Cl. .............................. 424/61; 424/401
[58] Field of Search .................. 424/61, 78.03, 424/63, 401; 252/364; 427/337

[56] References Cited

U.S. PATENT DOCUMENTS

| | | | |
|---|---|---|---|
| 1,878,103 | 9/1932 | Bradley . | |
| 4,146,499 | 3/1979 | Rosano | 252/186.32 |
| 4,511,554 | 4/1985 | Geria et al. | 424/65 |
| 5,219,560 | 6/1993 | Suzuki et al. | 424/63 |
| 5,468,477 | 11/1995 | Kumar et al. | 424/78.17 |
| 5,496,544 | 3/1996 | Mellul et al. | 424/78.03 |
| 5,549,930 | 8/1996 | Reysis | 427/337 |
| 5,643,581 | 7/1997 | Mougin et al. | 424/401 |

FOREIGN PATENT DOCUMENTS

| | | |
|---|---|---|
| 3-081214 | 4/1991 | Japan . |
| 3081214 | 5/1991 | Japan . |
| 91/08731 | 6/1991 | WIPO . |
| 92/00077 | 1/1992 | WIPO . |

OTHER PUBLICATIONS

French Search Report, dated Aug. 2, 1995.

*Primary Examiner*—Thurman K. Page
*Assistant Examiner*—Sharon Howard
*Attorney, Agent, or Firm*—Finnegan, Henderson, Farabow, Garrett & Dunner, L.L.P.

[57] ABSTRACT

A quick-drying agent for a film of nail varnish comprising at least one silicone oil and at least one solvent, the solvent comprising petroleum ether. A process for drying a film of nail varnish wherein the drying agent is applied to the film deposited on the nail. A cosmetic composition comprising a petroleum ether solvent, a silicone oil, and optionally an additional solvent, used to improve and accelerate the drying of a nail varnish film.

19 Claims, No Drawings

QUICK-DRYING AGENT FOR A NAIL VARNISH FILM AND DRYING PROCESS USING THE SAID AGENT

The present invention relates to a quick-drying agent for a nail varnish film. More precisely, this invention is a drying agent which, when applied to the surface of a layer of varnish on a nail, improves the drying rate thereof.

Nail varnishes generally comprise at least one film-forming agent, one plasticizer, one gelling agent, and one solvent. The film-forming agent may be nitrocellulose and/or a resin such as an alkyd, acrylic or polyurethane resin, or may result from the condensation of formaldehyde with an arylsulphonamide. The plasticizer may be camphor or a phthalate. The gelling agent may be bentonite, cellulose derivatives, and/or pyrogenous silicas. The solvent may be an alcohol such as ethanol, isopropanol or butanol, an acetate such as ethyl acetate or butyl acetate, a ketone, and/or a diluent such as an aliphatic and/or aromatic hydrocarbon.

Nail varnishes are generally applied, in one or more layers, to the nail surface, and the solvent is allowed to evaporate to deposit a film on the nail. Immediately after deposition, the layers of nail varnish risk being damaged by friction and/or attachment to foreign bodies. Therefore, drying these varnishes rapidly after application is desirable.

It is known that the drying rate can be optimized by selecting components based on their chemical nature and volatility. Components used in this optimization include those forming part of the nail varnish composition, including the solvent and possibly the diluent.

This optimization is restricted by the composition of the nail varnish because excessively volatile components can damage the quality of the make-up effect obtained. Volatile components may cause defects, such as lines forming on the layer of varnish, and those resulting from rapid drying of the brush, to appear during application of the nail varnish. These defects cause a film which is non-uniform, not sufficiently smooth, of little sheen, and of unsatisfactory staying power.

To improve the quality of nail make-up, it is common to use a quick-drying agent, or drying accelerator. The agent is applied to the film of varnish during drying to quickly produce a dry and hard, and thus manipulable, film of nail varnish.

Known drying agents are described in patent publications JP-A-01016710 and JP-A-03081214. These documents disclose use of silicone oils of low viscosities less than 20 mPa·s to obtain a drying agent which has good properties on application. These oils can diffuse rapidly and uniformly to the surface of the varnish film, have an efficient drying action on the varnish, and leave no residue on the film of varnish.

In the past, using oils of a high viscosity greater than 20 mPa·s did not result in a drying agent with good properties. In particular, it was difficult to obtain rapid and uniform spreading of the oils at the surface of the film of varnish due to the high viscosity of such oils. Furthermore, certain difficulties in application were at least sometimes encountered during the use of such oils.

In an effort to avoid these drawbacks, these silicone oils can be combined with fatty solvents, such as isopropyl myristate, and/or mineral oils, such as liquid petrolatum. The fatty solvents, however, do not, or only sparingly, solubilize the film of nail varnish. Because these solvents are slightly volatile, the resulting drying agent obtained is too greasy both when applied and when dried.

The present invention proposes a quick-drying agent for a film of nail varnish which contains low or high viscosity silicone oils. These agents can allow deposition of a screening film onto the nail without leaving a pronounced greasy effect on the nail, thereby limiting the risks of scratching and smearing of the varnish. The quick-drying agent comprises at least one silicone oil and at least one solvent, with the solvent comprising a petroleum ether.

Another subject of the invention is using a petroleum ether and a silicone oil in a cosmetic composition, which optionally comprises an additional solvent, to improve and/or accelerate the drying of a nail varnish film.

The drying agent obtained in accordance with the invention has good cosmetic properties and, upon application to a film of nail varnish, allows the rapid production of this film. The resulting film is dry and resists the risk of damage.

Another advantage of the drying agent according to the invention is that it may be applied to any type of varnish. In particular, the drying agent may be applied to a varnish in either a solvent or aqueous medium.

The petroleum ether according to the present invention is a very volatile mixture of saturated, straight, or branched hydrocarbons. It is generally obtained by distillation of refined petroleum fractions at temperatures in the range of 30° to 75° C. The petroleum ether, also known as ESSENCE G from Total, essentially contains a mixture of straight or branched C5–C6 alkanes, predominantly C5 alkanes. The petroleum ether is preferably used at a concentration ranging from 5 to 99%, more preferably 40–60%, by weight relative to the total weight of the drying agent.

The silicone oil according to the invention is not limited to any viscosity value. A volatile or non-volatile silicone oil may be used. There may be mentioned, for example, alone or as a mixture: cyclomethicones such as cyclomethicones D4, D5 and D6; polydimethylsiloxanes, preferably with a viscosity of less than 100 mPa·s; polydimethylsiloxanols; and alkyldimethicones corresponding to the formula (I):

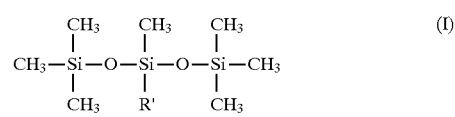

in which R' represents the radical $C_nH_{2n+1}$, with n=3–8.

The silicone oil may be a phenylated silicone oil. The oil may be a polyphenylmethylsiloxane, a phenyltrimethicone, or a mixture thereof, and particularly corresponds to the formula II:

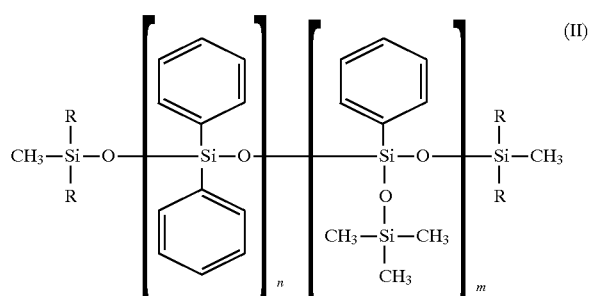

wherein: R, which can be identical or different, represents an alkyl radical containing 1 to 30 carbon atoms, an aryl radical, or an aralkyl radical; n represents a whole number in the range of 0 to 100; m represents a whole number in the range of 0 to 100, and the sum n+m is in the range of 1 to 100.

Preferably, R is a methyl, ethyl, propyl, isopropyl, decyl, dodecyl, octadecyl, phenyl, tolyl, benzyl, or a phenethyl radical.

Among these oils, mention may be made of the types commercialized under the trade names "ABIL AV 8853" by Goldschmidt, "DC 556" and "SF 558" by Dow Corning, "Silbione 70633 V 30" by Rhône-Poulenc, "SI 555" by Siss, and "Belisil PDM 1000" by Wacker.

The silicone oil may be used at a content in the range of 1% to 60%, preferably 15–30%, by weight relative to the total weight of the drying agent.

Preferably, the silicone oils have a viscosity greater than 20 mPa·s. More preferably, the viscosity is in the range of 25 to 10,000 mPa·s.

The drying agent according to the invention may comprise a silicone gum, which is optionally solubilized in a silicone oil. The silicone gum may be, alone or as a mixture, a gum of the formula (III):

$$X-\underset{R_2}{\overset{R_1}{Si}}-\left[O-\underset{R_4}{\overset{R_3}{Si}}\right]_n\left[O-\underset{R_6}{\overset{R_5}{Si}}\right]_p-O-\underset{R_2}{\overset{R_1}{Si}}-X \quad (III)$$

in which:

$R_1$, $R_2$, $R_5$, and $R_6$ are identical or different and represent an alkyl radical having 1 to 6 carbon atoms;

$R_3$ and $R_4$ are identical or different and represent an alkyl radical having from 1 to 6 carbon atoms or an aryl radical;

X is an alkyl radical having from 1 to 6 carbon atoms, a hydroxyl radical, or a vinyl radical;

and n and p are chosen so as to impart a viscosity of greater than 100,000 mPa·s, preferably greater than 500,000 mPa·s, to the silicone gum.

The silicone gum is preferably present at a concentration of 0–10% by weight.

Examples of silicone gum of the formula (III) used according to the invention are those wherein:

(1) $R_1$ to $R_6$ and X represent a methyl group, p=0, and n=2700, such as "SE30" sold by General Electric;

(2) $R_1$ to $R_6$ and X represent a methyl group, p=0, and n=2300, such as "AK 500000" sold by Wacker;

(3) $R_1$ to $R_6$ represent a methyl group, X represents a hydroxyl group, p=0, and n=2700, as a 13% solution in cyclopentasiloxane, such as "Q2-1401" sold by Dow Corning;

(4) $R_1$ to $R_6$ represent a methyl group, X represents a hydroxyl group, p=0, and n=2700, as a 13% solution in polydimethylsiloxane, such as "Q2-1403" sold by Dow Corning; and (5) $R_1$, $R_2$, $R_5$, $R_6$, and X represent a methyl group and $R_3$ and $R_4$ represent an aryl group, so that the molecular weight of the compound is 600,000, such as "761" sold by Rhône-Poulenc.

The drying agent according to the invention may comprise solvents in addition to petroleum ether. Such compounds should not, or should only sparingly, solubilize the film of varnish deposited on the nail. They should be compatible with the silicone oil and form only a single phase with the silicone oil used. Examples of these solvent compounds are isopropyl myristate, isobutane, isopropanol and/or ethanol, and mixtures thereof.

The drying agent according to the invention optionally contains cosmetic additives such as fragrances, dyes and/or pigments, and cosmetic active agents such as vitamins and/or UV screening agents.

The invention also relates to a process for drying a film of nail varnish, wherein a drying agent as described above is applied to the film deposited on the nail. The drying agent is preferably applied using a brush, vaporizer, or an aerosol spray.

The following examples illustrating the present invention, without limiting the scope thereof.

EXAMPLE 1

A drying agent with the following composition was prepared:

80 g of petroleum ether (ESSENCE G from Total) and 20g of decamethylcyclopentasiloxane (viscosity: 4 mPa·s).

The drying agent was applied to a film of nail varnish in a solvent medium. The agent was easy to apply, and the film obtained after application was not too greasy.

EXAMPLE 2

A drying agent having the following composition was prepared:

95 g of petroleum ether (ESSENCE G from Total), 4 g of octamethylcyclotetrasiloxane (viscosity: 7 mPa·s), and 1 gram of polydimethylsiloxanol mixed with cyclotetra- and cyclopentadimethylsiloxane (QC F2-1671 from Dow Corning).

The drying agent was applied to a film of nail varnish in a solvent medium. The film dried quickly and did not leave a pronounced greasy effect on the nail.

EXAMPLE 3

A drying agent having the following composition was prepared:

75 g of petroleum ether (ESSENCE G from Total), 10 g of isopropyl myristate, 10 g of decamethylcyclopentasiloxane (viscosity: 4 mPa·s), and 5 g of liquid petrolatum.

The drying agent was applied to a film of nail varnish in an aqueous medium. The film obtained after drying was not of a pronounced greasy nature.

EXAMPLE 4

A drying agent having the following composition was prepared:

67.6 g of petroleum ether (ESSENCE G from Total), 20 g of decamethylcyclopentasiloxane (viscosity: 4 mPa·s), 10 g of isopropyl myristate, 2 g of isopropanol, 0.3 g of UV screening agent, and 0.1 g of vitamins, fragrance, dye.

The drying agent was applied to a film of nail varnish in an aqueous medium. This film had the expected cosmetic properties according to the invention.

EXAMPLE 5

A drying agent packaged in the form of an aerosol spray having the following composition was prepared:

1.6 g of petroleum ether (ESSENCE G from Total), 1.2 g of decamethylcyclopentasiloxane (viscosity: 4 mPa·s), 1.2 g of isopropyl myristate, and 96 g of isobutane.

The drying agent was applied to a film of nail varnish in a solvent medium. This film had the expected cosmetic properties according to the invention.

EXAMPLE 6

A drying agent of the following composition was prepared:

98 g of petroleum ether (ESSENCE G from Total) and
2 g mixture of polydimethylsiloxanol (14%) and cyclotetra- and cyclopentadimethylsiloxane (QC F2-1671 from Dow Corning) (viscosity: 7000 mPa·s).

The drying agent was applied to a film of nail varnish in a solvent medium. The film dried quickly and did not leave a pronounced greasy effect on the nail.

What is claimed is:

1. A quick-drying agent for a film of nail varnish comprising at least one silicone oil and at least one solvent, wherein the solvent comprises petroleum ether.

2. The drying agent according to claim 1, wherein the silicone oil is selected from cyclomethicones, polydimethylsiloxanes, polydimethylsiloxanols, phenylated silicone, and alkyldimethicones corresponding to the formula (I)

$$CH_3-\underset{\underset{CH_3}{|}}{\overset{\overset{CH_3}{|}}{Si}}-O-\underset{\underset{R'}{|}}{\overset{\overset{CH_3}{|}}{Si}}-O-\underset{\underset{CH_3}{|}}{\overset{\overset{CH_3}{|}}{Si}}-CH_3 \qquad (I)$$

in which R' represents the radical $C_nH_{2n+1}$, with n=3–8.

3. The quick-drying agent according to claim 2, wherein the phenylated silicone oil is selected from polyphenylmethylsiloxanes, phenylatedtrimethicones, and phenylated silicone oils of the formula II $$CH_3-\underset{R}{\overset{R}{Si}}-O-\left[\underset{}{\overset{}{Si}}-O\right]_n-\left[\underset{O-Si(CH_3)_2CH_3}{\overset{}{Si}}-O\right]_m-\underset{R}{\overset{R}{Si}}-CH_3 \qquad (II)$$

wherein:

R, which can be identical or different, represents an alkyl radical containing 1 to 30 carbon atoms, an aryl radical, or an aralkyl radical;

n represents a whole number in the range of 0 to 100;

m represents a whole number in the range of 0 to 100; and the sum n+m is in the range of 1 to 100.

4. The drying agent according to claim 1 wherein the content of silicone oil is in the range of 1% to 60% by weight relative to the total weight of the agent.

5. The drying agent according to claim 4 wherein the content of silicone oil is in the range of 15 to 30% by weight relative to the total weight of the agent.

6. The drying agent according to claim 1 wherein the silicone oil has a viscosity above 20 mPa·s.

7. The drying agent according to claim 6, wherein the silicone oil has a viscosity in the range of 25 to 10,000 mPa·s.

8. The drying agent according to claim 1 wherein the content of petroleum ether is in the range of 5% to 99% by weight relative to the total weight of the agent.

9. The drying agent according to claim 8 wherein the content of petroleum ether is in the range of 40 to 60% by weight relative to the total weight of the agent.

10. The drying agent according to claim 1 further comprising at least one silicone gum.

11. The drying agent according to claim 10 wherein the silicone gum is selected, alone or as a mixture, from the gums corresponding to the formula (III):

$$X-\underset{\underset{R_2}{|}}{\overset{\overset{R_1}{|}}{Si}}-\left[O-\underset{\underset{R_4}{|}}{\overset{\overset{R_3}{|}}{Si}}\right]_n-\left[O-\underset{\underset{R_6}{|}}{\overset{\overset{R_5}{|}}{Si}}\right]_p-O-\underset{\underset{R_2}{|}}{\overset{\overset{R_1}{|}}{Si}}-X \qquad (III)$$

in which:

$R_1$, $R_2$, $R_5$, and $R_6$ are, together or separately, an alkyl radical having 1 to 6 carbon atoms;

$R_3$ and $R_4$ are, together or separately, an alkyl radical having 1 to 6 carbon atoms, or an aryl radical;

X is an alkyl radical having 1 to 6 carbon atoms, a hydroxyl radical, or a vinyl radical; and n and p are chosen to impart a viscosity of greater than 100,000 mPa·s to the silicone gum.

12. The drying agent according to claim 10 wherein the content of the silicone gum is in the range of 1 to 10% by weight.

13. The drying agent according to claim 1 comprising at least one compound, other than petroleum ether, as a solvent.

14. The drying agent according to claim 13, wherein said at least one compound is isopropyl, myristate, isobutane, isopropanol, or ethanol.

15. The drying agent according to claim 1 further comprising at least one cosmetic additive, at least one cosmetic active agent, or a mixture of said at least one cosmetic additive and said at least one cosmetic active agent.

16. A process for drying a film of nail varnish, comprising the step of applying a drying agent according to claim 1 to the film deposited on the nail.

17. A process for accelerating or improving the drying of a film of nail varnish comprising the step of applying a drying agent according to claim 1 to the film deposited on the nail to accelerate or improve the drying of said film.

18. A cosmetic composition comprising a petroleum ether solvent, a silicone oil, and optionally an additional solvent.

19. A composition comprising a film of nail varnish and, in contact with said film, at least one silicone oil and at least one solvent, wherein the solvent comprises petroleum ether.

* * * * *